United States Patent [19]

Schönafinger et al.

[11] 4,356,178
[45] Oct. 26, 1982

[54] 3,4-(BIS-SUBSTITUTED)-1,2,5-OXDIAZOLE 2-OXIDES, THEIR USE AND PHARMACEUTICAL FORMULATIONS CONTAINING THEM

[75] Inventors: Karl Schönafinger; Rudi Beyerle; Anton Mogilev, all of Frankfurt am Main; Helmut Bohn; Melitta Just, both of Schöneck; Piero A. Martorana, Bad Homburg; Rolf-Eberhard Nitz, Frankfurt am Main, all of Fed. Rep. of Germany

[73] Assignee: Cassella Aktiengesellschaft, Frankfurt am Main, Fed. Rep. of Germany

[21] Appl. No.: 332,234

[22] Filed: Dec. 18, 1981

[30] Foreign Application Priority Data

Dec. 18, 1980 [DE] Fed. Rep. of Germany ....... 3047730

[51] Int. Cl.³ .................. A61K 31/535; A61K 31/42; C07D 413/14
[52] U.S. Cl. ......................... 424/248.54; 424/248.55; 424/248.57; 424/250; 424/267; 424/272; 544/82; 544/138; 544/357; 544/367; 546/187; 546/209; 260/245.5; 548/125
[58] Field of Search ............... 544/138, 82, 367, 357; 546/209, 187; 260/245.5; 424/248.57, 248.54, 248.55, 267, 272, 250; 548/125

[56] References Cited

U.S. PATENT DOCUMENTS 4,089,867  5/1978  Duranleau et al. ................. 548/125

OTHER PUBLICATIONS

Schoenafinger et al., *Chemical Abstracts*, vol. 96, (1981), No. 40909s.
Grundman et al., *Chemical Abstracts*, vol. 88, (1975), No. 50732c.

*Primary Examiner*—Robert W. Ramsuer
*Attorney, Agent, or Firm*—Berman, Aisenberg & Platt

[57] ABSTRACT

Pharmacologically-valuable 3,4-(bis-substituted)-1,2,5-oxdiazole 2-oxides of formula I

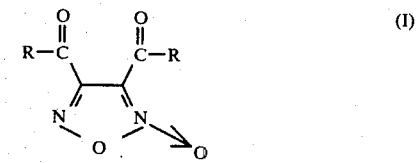

[wherein R denotes $-NHR^1$, $-NR^2R^3$, $-NHR^4OR^2$, $-NHR^5COR^6$ or

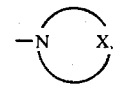

$R^1$ denotes alkyl having from 1 to 6 C atoms or cycloalkyl having 4 to 7 ring C atoms, $R^2$ and $R^3$ denote alkyl having from 1 to 4 C atoms, $R^4$ denotes an alkylene radical of the formula $-C_nH_{2n}-$ (wherein n denotes 2, 3 or 4), $R^5$ denotes an alkylene radical of the formula $-C_mH_{2m}-$ (wherein m denotes 1, 2 or 3), $R^6$ denotes $-OR^2$, $-NHR^1$, $-NR^2R^3$ or $-NH_2$, X denotes $-(CH_2)_p-$, $-(CH_2)_2-O-(CH_2)_2-$ or

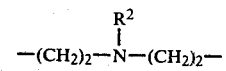

and p is 4, 5 of 6] and their pharmacologically-acceptable acid-addition compounds are prepared by elimination of hydrogen chloride from a hydroxamoyl chloride of the formula $$R-CO-C(Cl)=NOH \qquad (II)$$

and dimerization. If desired, the resulting reaction product is subsequently converted into an acid-addition compound. The compounds and pharmaceutical preparations thereof are useful for treating and for prophylaxis of cardiovascular diseases.

16 Claims, No Drawings

3,4-(BIS-SUBSTITUTED)-1,2,5-OXDIAZOLE 2-OXIDES, THEIR USE AND PHARMACEUTICAL FORMULATIONS CONTAINING THEM

Related Application: This application is related to a concurrently-filed application Ser. No. 332,237, the entire disclosure of which is incorporated herein by reference.

The invention relates to 3,4-(bis-substituted)-1,2,5-oxdiazole 2-oxides of the formula

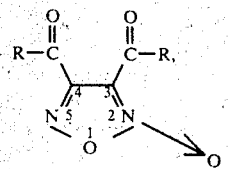

wherein
R denotes —NHR$^1$, —NR$^2$R$^3$, —NHR$^4$OR$^2$, —NHR$^5$COR$^6$ or

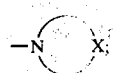

R$^1$ denotes alkyl having from 1 to 6 C atoms or cycloalkyl having from 4 to 7 ring C atoms;
each of
R$^2$ and R$^3$, independently, denotes alkyl having from 1 to 4 carbon atoms;
R$^4$ denotes alkylene of the formula —C$_n$H$_{2n}$—;
n denotes 2, 3 or 4;
R$^5$ denotes alkylene of the formula —C$_m$H$_{2m}$—;
m denotes 1, 2 or 3;
R$^6$ denotes —OR$^2$, —NHR$^1$, —NH$_2$ or —NR$^2$R$^3$;
X denotes —(CH$_2$)$_p$—, —(CH$_2$)$_2$—O—(CH$_2$)$_2$— or

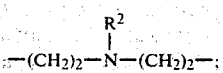

p is 4, 5 or 6;
and their pharmaceutically-acceptable acid-addition salts, a process for their preparation, their use as pharmacologically-active compounds and pharmaceutical formulations containing them.

The alkyl radicals represented by R$^1$, R$^2$ and R$^3$ and also the alkylene radicals represented by R$^4$ are straight-chain or branched. Preferred compounds of formula I are those wherein R contains an —NH— grouping. R$^4$ preferably represents —(CH$_2$)$_2$— or —(CH$_2$)$_3$—, and R$^5$ preferably represents —CH$_2$— or —(CH$_2$)$_2$—. R$^2$ preferably denotes methyl or ethyl.

The compounds of formula I are prepared, e.g., from hydroxamoyl chlorides of formula II by elimination of HCl and subsequent dimerization:

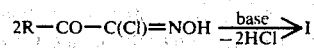

The reaction is carried out in a suitable solvent or dispersing agent, such as dimethylformamide, dimethyl sulfoxide, N-methylpyrrolidone or a lower alcohol, e.g., methanol or ethanol, but preferably in water. Mixtures of different solvents or dispersing agents, in particular homogeneous and also heterogeneous mixtures with water, such as water/methanol or water/diethyl ether, are optionally used. In general, the reaction is carried out at from 0° to +50° C., preferably at from 10° to 25° C.

The reaction frequently takes place by itself after compound II is introduced into the solvent or dispersing agent. However, it is accelerated considerably by adding a base which binds eliminated hydrogen chloride. The following are examples of useful bases of this type: secondary or tertiary organic amines, such as dimethylamine, trimethylamine, diethylamine, triethylamine or pyridine; alkali-metal hydroxides, such as sodium hydroxide or potassium hydroxide; alkali-metal carbonates and alkali-metal bicarbonates, such as potassium carbonate, sodium carbonate and sodium bicarbonate; and alkali-metal acetates, such as sodium acetate. Sodium carbonate and sodium bicarbonate are preferred. The base is optionally added [in the form of a solution (for example an aqueous solution as in the case of a lower organic amine) or a dispersion] to a solution or dispersion of compound II. In view of the nature of the reaction which takes place, the base is appropriately added gradually or in portions while stirring the reaction mixture. The base is preferably added in a molar quantity (2 mols of base for 2 mols of compound II) or, if appropriate, in an excess of up to 20 molar percent. When the reaction is complete, the compound of formula I which has been formed is separated off and, if desired, is converted into an acid-addition salt.

The required hydroxamoyl chloride starting compounds of formula II are prepared by known processes (from available starting materials or from corresponding materials which are readily synthesized according to established reactions), for example by first reacting diketene III with an amine IV to give an acetoacetamide V (compare, for example, U.S. Pat. No. 2,174,239):

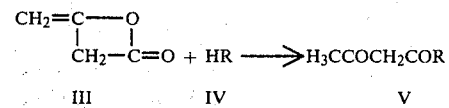

The reaction between compounds III and IV is carried out in a suitable solvent, such as water or an alcohol, e.g. a lower alkanol, normally at temperatures from 10° to 50° C., preferably at room temperature.

The acetoacetamide V is oximated in a suitable solvent, such as water, glacial acetic acid or an alcohol, by means of nitrous acid produced in situ, the oxime VI being formed:

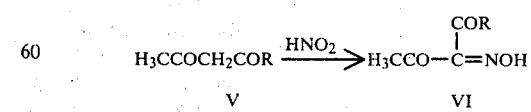

This reaction is carried out, for example, at a pH value of not less than 4.0 and at temperatures from 10° to 50° C., preferably at room temperature.

The nitrous acid is most simply produced from sodium nitrite and hydrochloric acid.

The oxime VI is then chlorinated in a suitable solvent, such as water or an alcohol, for example at temperatures from +10° to 70° C., preferably from 30° to 50° C., the hydroxamoyl chloride II being formed.

The hydroxamoyl chloride II is alternatively prepared from the acetoacetamide V by reversing the sequence of the oximation and chlorination reactions. In the chlorination reaction, chlorine compound VII: $CH_3COCHClCOR$, is then first formed from the acetoacetamide V and is then converted into compound II by reaction with nitrous acid.

The conversion of acetoacetamides V into compounds of formula III is described, for example, in German Auslegeschrift No. 1,963,061. Starting from diketene III and amine IV, compounds according to the invention are optionally prepared by previously noted stages of synthesis in a single reaction vessel without isolating the intermediate products. The yields, calculated over all the steps, are generally from 20 to 70 percent of theory.

The hydroxamoyl chlorides II are optionally prepared by reacting a glyoxylic acid ester-oxime VII with an amine IV, the oxime compound VIII being formed first.

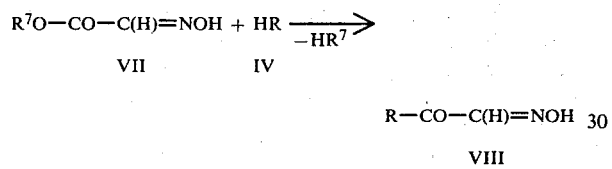

$$R^7O-CO-C(H)=NOH + HR \xrightarrow[-HR^7]{} R-CO-C(H)=NOH$$
$$\text{VII} \qquad \text{IV} \qquad\qquad \text{VIII}$$

wherein $R^7$ denotes lower alkyl, particularly methyl or ethyl. Compound VIII is then converted into compound II by chlorination.

Compounds I, which have a basic side chain, form salts with inorganic or organic acids. The following are examples of such acids: hydrochloric acid, hydrobromic acid, phosphoric acid, sulfuric acid, oxalic acid, lactic acid, tartaric acid, acetic acid, salicylic acid, benzoic acid, citric acid, ascorbic acid, adipic acid and naphthalene-disulfonic acid. The acid-addition salts are obtained in known manner by combining the components in a suitable solvent or dispersing agent. Acid-addition salts which are not pharmacologically acceptable are readily converted by known procedures to the corresponding free base or to pharmaceutically-acceptable acid-addition salts.

The compounds of formula I and their pharmacologically-acceptable acid-addition salts possess valuable pharmacological properties. Their action on the heart circulation system is particularly pronounced. In low dosages they lower blood pressure, reduce peripheral resistance and produce a reduction in heart action via a lowering of pulmonary arterial pressure at a pulse rate which is only slightly affected.

The compounds of formula I and their pharmacologically-acceptable acid-addition salts are, therefore, administerable to humans as drugs on their own, as mixtures with one another or in the form of pharmaceutical formulations which permit enteral or parenteral administration and which contain, as the active constituent, an effective dose of at least one compound of formula I or an acid-addition salt thereof, together with customary excipients and additives, which are pharmaceutically unobjectionable.

The drugs are administered orally, for example in the form of pills, tablets, lacquered tablets, dragees, hard and soft gelatin capsules, solutions, syrups, emulsions or suspensions or aerosol mixtures. Administration, however, is alternatively carried out rectally, for example in the form of suppositories; parenterally, for example in the form of injection solutions; or percutaneously, for example in the form of an ointment or tincture.

Pharmaceutical formulations are prepared, e.g., with pharmaceutically-inert inorganic or organic excipients. Lactose, maize starch or derivatives thereof, talc, stearic acid or salts thereof are, e.g., used for the preparation of pills, tablets, dragees and hard gelatin capsules. Excipients for soft gelatin capsules and suppositories are, for example, fats, waxes, semi-solid and liquid polyols, natural or hardened oils and the like. Examples of suitable excipients for the preparation of solutions and syrups are water, sucrose, invert sugar, glucose, polyols and the like. Examples of suitable excipients for the preparation of injection solutions are water, alcohols, glycerol, polyols, vegetable oils and the like.

In addition to the active compounds and excipients, the pharmaceutical formulations optionally also contain additives, such as fillers, extenders, disintegrants, binders, lubricants, wetting agents, stabilizers, emulsifying agents, preservatives, sweeteners, colorants, flavoring agents or flavorings, thickeners, diluents, buffer substances and also solvents or solubilizers or agents for achieving a depot effect, and also salts for altering osmotic pressure, coating agents or antioxidants. They alternatively contain two or more compounds of formula I or pharmacologically-acceptable acid-addition salts thereof and, optionally, other therapeutically-active substances.

The following are examples of other suitable therapeutically-active substances: β-receptor blockers, such as propranolol, pindolol or metoprolol; vasodilators, such as carbochromen; sedatives, such as barbituric acid derivatives, 1,4-benzodiasepines and meprobamate; diuretics, such as chlorothiazide; heart tonics, such as digitalis formulations; agents which lower blood pressure, such as hydralazine, dihydralazine, prazosin, clonidine or Rauwolfia alkaloids; agents which lower fatty acid level in the blood, such as bezafibrate or fenofibrate; and agents for prophylaxis of thrombosis, such as phenprocoumon.

Compounds of formula I, their pharmacologically-acceptable acid-addition salts and pharmaceutical formulations, which contain compounds of formula I or their pharmacologically-acceptable acid-addition salts as active compounds, are useful for humans in combating or preventing diseases of the cardiovascular system, for example as anti-hypertensive drugs against various forms of high blood pressure, and in combating or preventing angina pectoris and the like. Suitable dosages vary within wide limits and are adapted in each particular case to individual factors. In general, a daily dose of from about 0.2 to 150 mg, preferably from 1 to 30 mg, per human individual is appropriate for oral administration. In the case of other administration forms too, owing to good absorption of the active compounds, the daily dose is within similar ranges, i.e. generally from 0.2 ro 150 mg/person. The daily dose is normally subdivided into several, for example 2 or 3, part administrations.

The pharmaceutical formulations generally contain from 0.1 to 50 mg/dose, preferably from 0.5 to 10 mg/dose, of active compound of formula I or a pharmacologically-acceptable acid-addition salt thereof.

Investigations into anti-anginal and anti-hypertensive action of compounds of formula I were conducted on mongrel dogs of both sexes under pentobarbital anaesthesia (30 to 40 mg/kg intravenously) or under urethane-chloralose anaesthesia (3 ml/kg of urethane-chloralose mixture administered intravenously = 20 mg/kg of chloralose and 250 mg/kg of urethane). Artificial respiration of the animals was effected by means of a Bird Mark 7 respirator. The final expiratory content of carbon dioxide (determined by means of the Uras) was between 4.5 and 5 percent by volume. During the entire experiment, the animals under pentobarbital anaesthesia received a continuous intravenous infusion of pentobarbital, 4 mg/kg/6 ml/hour, in order to ensure a constant depth of anaesthesia; the animals under urethane-chloralose anaesthesia did not receive a continuous infusion. The infusion was administered through the cephalic vein. After the experimental animal had been prepared, there was a waiting period of approximately 1 hour until all haemodynamic parameters had stabilized (steady state). The actual test was then begun.

The systolic and diastolic blood pressure was determined peripherally in the femoral artery via a Statham pressure recorder. A Millar tip catheter inserted via the carotid artery into the left ventricle provided the signal for the LVEDP (left ventricular end diastolic pressure) and the pulse rate. The average blood pressure in the pulmonary artery was determined by means of a second tip catheter inserted via the jugular vein. The results obtained are shown in the table below:

$$R-\overset{\overset{O}{\|}}{C}-\underset{\underset{\underset{O}{\searrow}}{N}}{\overset{\|}{\underset{}{}}}\overset{\overset{O}{\|}}{C}-R$$

(structure: 1,2,5-oxadiazole-2-oxide-3,4-bis-(carboxylic acid amide))

| R | Dose mg/kg | LVEDP Δ mmHg | PAP Δ mmHg | BPa Δ mmHg | PR Δb/minute | T /minutes |
|---|---|---|---|---|---|---|
| —NHCH₂CHCH₃<br>  \|<br>  CH₃ | 0.05 | −2 | −3 | −70 | — | 60 |
| —NH—cyclohexyl | 0.05 | −3.5 | −3 | −65 | −5 | 45 |
| —NHCHCH₃<br>  \|<br>  CH₂CH₃ | 0.05 | −2 | −3 | −75 | −10 | 75 |
| —NH—C(CH₃)₃ | 0.05 | −2 | −2 | −60 | +5 | 60 |
| —NHCH₂CO₂CH₃ | 0.05 | −5 | −3 | −65 | +10 | 45 |
| —NHCH₂CH₃ | 0.05 | −7 | −3 | −85 | −5 | 60 |
| piperidino | 0.05 | — | −1 | −25 | −20 | >120 |
| —NHC₄H₉(n) | 0.05 | −5 | −2.5 | −70 | −10 | 30 |
| —N(CH₂CH₃)₂ | 0.1 | −2.5 | −1 | −25 | −5 | 35 |
| —NHCH₂CH₂OCH₃ | 0.05 | −4 | −1.5 | −65 | +30 | 40 |
| —NH—CH(CH₃)—CH₃ | 0.05 | −2.3 | −1.5 | −45 | −1 | 75 |
| —NHCH₃ | 0.05 | −7 | −4 | −55 | −15 | 60 |
| ISDN | 0.05 | −2.1 | −0.7 | −19 | ±0 | 30 |

The abbreviations in the table have the following meanings:
LVEDP = left ventricular end diastolic pressure
PAP = average pulmonary arterial pressure
BPa = average peripheral blood pressure
PR = pulse rate (b = beats)
T = average duration of action
ISDN = isosorbide dinitrate (comparison substance)

The following example serves to illustrate the invention further.

EXAMPLE 1,2,5-Oxadiazole-2-oxide-3,4-bis-(carboxylic acid methylamide).

12.5 g of methylamine are dissolved in 400 ml of water. 34 g of diketene are slowly added dropwise at room temperature (20° C.), a stable pH value of 7 being established. 28 g of sodium nitrite are then dissolved in the resulting solution. 40 g of concentrated hydrochloric acid are then added dropwise at such a rate that the pH value of the solution does not fall below 4. Stirring is then continued for a further 30 minutes, and 30 g of chlorine are then passed in at from 20° to 40° C. After the solution has cooled, it is cooled to −10° C.; resulting solids are filtered off. They are suspended in 100 ml of water, and a total of 33.6 g of sodium bicarbonate is added cautiously, in portions, at 20° C. The solution now has a pH value of from 7.5 to 8. It is now cooled to 0° C.; precipitated solids are filtered off and recrystallized from isopropanol to obtain the title compound as colorless crystals (melting point: 164° to 165° C.).

The 1,2,5-Oxadiazole-2-oxide-3,4-bis-carboxylic acid amides of the following table can be prepared in a corresponding manner.

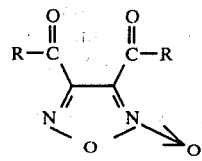

wherein
R is —NHR$^1$, —NR$^2$R$^3$, —NHR$^4$OR$^2$, —NHR$^5$COR$^6$ or

| 1,2,5-Oxidazole-2-oxide-3,4-bis-carboxylic acid amide | Melting Point in °C. | Reaction Temperature in °C. | Solvent | Base |
|---|---|---|---|---|
| Bis-dimethylamide | 127–129 | 30 | H$_2$O | NaHCO$_3$ |
| Bis-diethylamide | Oil | 35 | H$_2$O | NaHCO$_3$ |
| Bis-morpholide | 127–139 | 30 | H$_2$O | NaHCO$_3$ |
| Bis-butylamide | 91–92 | 25 | H$_2$O/C$_2$H$_5$OC$_2$H$_5$ | NaHCO$_3$ |
| Bis-pyrrolidide | 106–108 | 30 | (CH$_3$)$_2$SO | Na$_2$CO$_3$ |
| Bis-ethylamide | 116–117 | 0 | DMF | KHCO$_3$ |
| Bis-isopropylamide | 128–131 | 20 | H$_2$O | (i-C$_3$H$_7$)$_2$NH |
| Bis-(2-methoxiethyl)amide | 94–95 | 10 | C$_2$H$_5$OH | CH$_3$COONa |
| Bis-piperidide | 115–116 | 25 | H$_2$O | CH$_3$COOK |
| Bis-tert.-butylamide | 166–167 | 50 | CH$_3$OH | (CH$_3$)$_3$N |
| Bis-cyclohexylamide | 137–139 | 45 | H$_2$O/C$_2$H$_5$OC$_2$H$_5$ | NaOH |
| Bis-isobutylamide | 83,5–87 | 10 | NMP | K$_2$CO$_3$ |
| Bis-se-butylamide | Oil | 10 | NMP | NaHCO$_3$ |
| Bis-(methoxicarbonylmethyl)amide | 97–99 | 20 | CH$_3$OH | KOH |
| Bis-cyclopentylamide | 114–146 | 30 | H$_2$O/C$_2$H$_5$OH | NaHCO$_3$ |
| Bis-propylamide | 117–118 | 20 | H$_2$O | NaHCO$_3$ |
| Bis-(4-methyl)piperazide | 240 (Degradation) Dihydrochloride | 25 | C$_2$H$_5$OH | NaHCO$_3$ |
| Bis-(3-methoxipropyl)amide | 65–68 | 10 | H$_2$O | NaHCO$_3$ |
| Bis-(4-methoxibutyl)amide | Oil | 20 | H$_2$O | NaHCO$_3$ |
| Bis-hexamethylenimide | 103–106 | 25 | H$_2$O/C$_2$H$_5$OC$_2$H$_5$ | NaHCO$_3$ |
| Bis-(2-methoxicarbonylethyl)amide | 80–82 | 10 | CH$_3$OH | NaHCO$_3$ |
| Bis-(2-methoxicarbonylpropyl)amide | Oil | 20 | CH$_3$OH | K$_2$CO$_3$ |
| Bis-(diethylaminocarbonylmethyl)amide | Oil | 25 | n-C$_3$H$_7$OH | K$_2$CO$_3$ |
| Bis-(aminocarbonylmethyl)amide | 141–142 | 20 | CH$_2$OH | NaHCO$_3$ |
| Bis-(di-n-butyl)amide | Oil | 30 | H$_2$O/C$_2$H$_5$OC$_2$H$_5$ | NaHCO$_3$ |
| Bis-(ethylaminocarbonyl)methyl)amide | Oil | 25 | H$_2$O | NaHCO$_3$ |
| Bis-(2-ethoxiethyl)amide | Oil | 20 | H$_2$O/C$_2$H$_5$OC$_2$H$_5$ | NaHCO$_3$ |
| Bis-(2-ethoxicarbonylethyl)amide | Oil | 20 | C$_2$H$_5$OH | K$_2$CO$_3$ |

DMF = Dimethylformamide
NMP = N—Methylpyrrolidone

The structures of synthesized compounds can be confirmed by elementary analysis and by their IR and NMR spectra.

The invention and its advantages are readily understood from the foregoing description. Various changes may be made in the synthesis, in the compounds, in the compositions and in the method of use without departing from the spirit and scope of the invention or sacrificing its material advantages. The previously-described embodiments are merely illustrative.

What is claimed is:
1. A 3,4-(bis-substituted)-1,2,5-oxdiazole 2-oxide of the formula

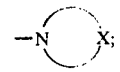

R$^1$ is alkyl having from 1 to 6 carbon atoms or cycloalkyl having from 4 to 7 ring carbon atoms;
each of
R$^2$ and R$^3$ is, independently, alkyl having from 1 to 4 carbon atoms;
R$^4$ is alkylene of the formula —C$_n$H$_{2n}$—;
R$^5$ is alkylene of the formula —C$_m$H$_{2m}$—;
R$^6$ is —OR$^2$, —NHR$^1$, —NR$^2$R$^3$ or —NH$_2$;
X is —(CH$_2$)$_p$—, —(CH$_2$)$_2$—O—(CH$_2$)$_2$— or —(CH$_2$)$_2$—N(R$^2$)—(CH$_2$)$_2$—;
m is 1, 2 or 3;
n is 2, 3 or 4; and
p is 4, 5 or 6;

or a pharmacologically-acceptable acid-addition salt thereof.

2. A compound according to claim 1 wherein R is —NHR$^1$.

3. A compound according to claim 1 wherein R is —NR$^2$R$^3$.

4. A compound according to claim 1 wherein R is —NHR$^4$OR$^2$.

5. A compound according to claim 1 wherein R is —NHR$^5$COR$^6$.

6. A compound according to claim 1 wherein R is

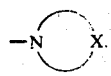

7. A compound according to claim 6 wherein X is —(CH$_2$)$_p$—.

8. A compound according to claim 6 wherein X is —(CH$_2$)$_2$—O—(CH$_2$)$_2$—.

9. A compound according to claim 6 wherein X is —(CH$_2$)—N(R$^2$)—(CH$_2$)$_2$—.

10. A compound according to claim 1 wherein R contains an —NH— grouping.

11. A compound according to claim 1 wherein R$^4$ is —(CH$_2$)$_2$— or —(CH$_2$)$_3$—.

12. A compound according to claim 1 wherein R$^5$ is —CH$_2$— or —(CH$_2$)$_2$—.

13. A compound according to claim 1 wherein R$^2$ is methyl or ethyl.

14. A method for treating or for prophylaxis of human cardiovascular-system disease which comprises administering an effective amount of a compound according to one of claims 1 and 10 to 13 to a human afflicted with or prone to such disease.

15. A pharmaceutical formulation of active ingredient and pharmacologically-compatible excipient, the active ingredient comprising a compound according to one of claims 1 and 10 to 13 in an amount of from 0.1 to 50 milligrams per unit dose.

16. A pharmaceutical formulation for treating or for prophylaxis of cardiovascular system disease which comprises a combination of pharmacologically-compatible excipient with an effective amount per unit dose of a compound according to one of claims 1 and 10 to 13.

* * * * *